United States Patent
Angus

(10) Patent No.: US 7,700,743 B2
(45) Date of Patent: Apr. 20, 2010

(54) IMMOBILISED AFFINITY MEDIUM AND ITS USE IN SEPARATION

(75) Inventor: Katherine Louise Angus, Washington (GB)

(73) Assignee: Millipore Corporation, Billierca, MA (US)

( * ) Notice: Subject to any disclaimer, the term of this patent is extended or adjusted under 35 U.S.C. 154(b) by 279 days.

(21) Appl. No.: 10/863,379

(22) Filed: Jun. 8, 2004

(65) Prior Publication Data

US 2005/0020812 A1 Jan. 27, 2005

(30) Foreign Application Priority Data

Jul. 22, 2003 (GB) .................................. 0317132.9
Sep. 25, 2003 (GB) .................................. 0322487.0

(51) Int. Cl.
*C07K 16/00* (2006.01)
*C07K 1/22* (2006.01)

(52) U.S. Cl. .................... 530/390.5; 210/660; 210/679; 210/690; 210/691; 422/69; 530/413; 530/415

(58) Field of Classification Search ................. 210/660, 210/679, 690, 691; 422/69; 424/177.1; 530/387.1, 530/390.5, 413, 415; 604/501
See application file for complete search history.

(56) References Cited

U.S. PATENT DOCUMENTS

| 4,861,705 A | 8/1989 | Margel |
| 5,053,332 A | 10/1991 | Cook |
| 5,652,348 A | 7/1997 | Burton |
| 5,945,520 A | 8/1999 | Burton |
| 6,117,996 A * | 9/2000 | Lowe et al. .................. 544/216 |
| 6,498,236 B1 | 12/2002 | Lihme et al. ............. 530/387.1 |
| 6,702,943 B1 * | 3/2004 | Johansson et al. ........... 210/635 |
| 2003/0187227 A1 * | 10/2003 | Lihme et al. ............. 530/387.1 |

FOREIGN PATENT DOCUMENTS

| WO | WO 90/09237 | 8/1990 |
| WO | WO 90/09238 | 8/1990 |
| WO | WO 97/10887 | 3/1997 |
| WO | WO 98/08603 | 3/1998 |
| WO | WO 98/58732 | 12/1998 |
| WO | WO 01/38227 A2 * | 5/2001 |

OTHER PUBLICATIONS

Hackh's Chemical Dictionary, McGraw-Hill, Inc., 1969, pp. 736-737.*

* cited by examiner

*Primary Examiner*—David A Saunders

(57) ABSTRACT

A chromatography media such as silica controlled pore glass or agarose containing an affinity ligand such as 2-Aminobenzimidazole (ABI) or aminomethylbenzimidazole (AMBI). The ligand is present in density of from about 30 to about 80 µmole/ml.

14 Claims, 1 Drawing Sheet

IMMOBILISED AFFINITY MEDIUM AND ITS USE IN SEPARATION

FIELD OF THE INVENTION

Figure 1:
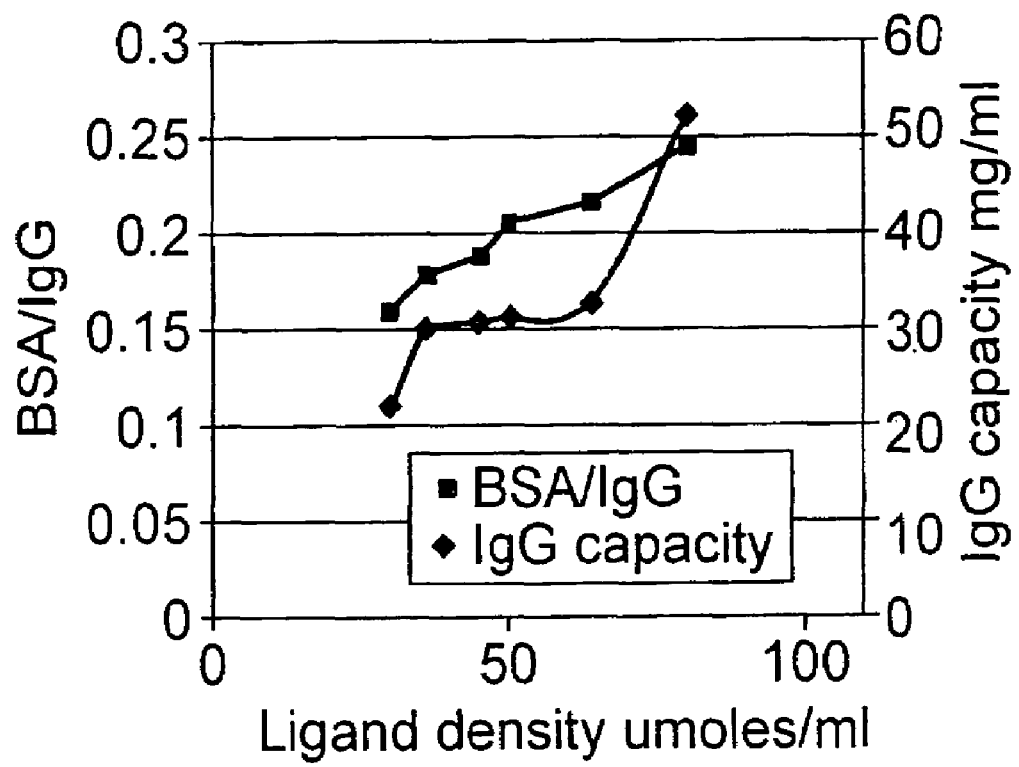

This invention relates to a medium and its use in separation.

BACKGROUND OF THE INVENTION

Affinity chromatography may be used for the purification of proteins, for example IgG purification. Affinity chromatography media typically comprise a solid support (e.g. a resin) and, attached thereto, a selection of affinity ligands. The selectivity of the ligands typically depends on a number of factors, for example the pH or ionic strength of the sample undergoing separation. The ionic strength or pH may be varied to enhance selectivity for a particular protein.

2-Aminobenzimidazole (ABI) and aminomethylbenzimidazole (AMBI) are examples of affinity chromatography ligands.

Judicious selection of the solid support, ligands and separation conditions allow a reasonable degree of specificity to be attained. However, conventional non-affinity chromatographic processes are typically accompanied by a high degree of non-specific binding. There remains a need for chromatography media having a greater degree of selectivity, particularly towards proteins such as IgG.

SUMMARY OF THE INVENTION

The present invention is based on the discovery that when ABI and/or AMBI are applied at a density of about 30 to about 80 μmole/ml and less than about 1 mmole/g (dry weight) to a solid substrate, optimum ligand performance is achieved.

A first aspect of the invention is a medium which comprises a solid support and, attached thereto, one or more ligands selected from ABI and AMBI, wherein the ligand density is from about 30 to about 80 μmole/ml and less than about 1 mmole/g.

A second aspect of the invention is a method for separating a compound from a sample, the compound capable of binding to ABI and/or AMBI, the method comprising contacting the sample with a medium of the invention.

Another aspect of the invention is a method for the manufacture of a medium of the invention, which comprises applying to a solid support, one or more ligands selected from ABI and AMBI.

DESCRIPTION OF THE INVENTION

The term "ABI" as used herein refers to 2-aminobenzimidazole.

The term "AMBI" as used herein refers to aminomethylbenzimidazole.

A medium of the invention may be obtained by any suitable method known in the art. For example, the medium may be obtained by activating or derivatising the surface of a porous support and then applying one or more ligands to the surface (see, for example, WO-A-98/080603, WO-A-90/09238 and WO-A-90/09237). Optionally, a spacer may be used between the support and a ligand.

Typically, a solvent or wetting agent (e.g. water) is used to apply ligands to the support. Rigid media (e.g. silica) hold any wetting agent within their pores. However, soft media (e.g. agarose gel) also expand upon exposure to the wetting agent. For this reason, two measures of ligand densities are used to define the invention: "μmole/ml" and "mmole/g".

The normal unit of measure is "μmole/ml". This unit represents the amount of ligand per total expanded volume, and relates directly to the ligand density of the support "in use".

To account for the variations between hard and soft media, ligand density is also expressed in units of "mmole/g". This unit of measure is equal to the amount of ligand per unit dry weight of media, thus eliminating the contribution of the wetting agent from the density comparison. For swelled gel media, this dry weight has a significantly different volume than the wetted media.

The solid support may be any suitable support known in the art. The support preferably comprises one or more caustic-resistant materials.

Caustic is commonly used in the biopharmaceutical industry as a cleanser and/or sanitant. It has been used to clean media between uses, ridding them of any contaminants that might otherwise remain. A caustic solution (used at typical conditions of 0.5M for 1 hour) may be used to inactivate any microbes or viruses that may remain. A problem with most current affinity ligands and some media (such as Protein A on controlled pore glass) is that the ligand as well as the support are often not caustic stable. Consequently, a degradation of performance may occur upon exposure to caustic. Acid rinses are sometimes used instead to avoid degradation, but these are not preferred.

Thus, it is preferred that the support is caustic stable. Examples of caustic-resistant materials include agarose, cellulose, zirconia, polyethylene, polypropylene, polytetrafluoroethylene (PTFE), polyethersulphone (PES) and polyvinylidene fluoride (PVDF). In a preferred embodiment, the support comprises cross-linked agarose, the proportion of agarose preferably from about 4 to about 8%, more preferably about 6%.

The support may be in any suitable form, for example in the form of one or more beads, membranes, non-woven sheets or monolithic structures. The support may be in the form of one or more porous beads.

Preferred supports include PVDF membranes (e.g. Durapore@), PES membranes (e.g. Express@), agarose beads, PTFE resins for filters or bead manufacture, non-wovens (e.g. Typar or Tyvec polyethylene) and PTFE membranes. Examples of agarose beads are described in U.S. Pat. Nos. 4,861,705, 5,053,332 and WO-A-98/58732.

Attached to the support are one or more ligands selected from ABI and AMBI. It is preferred that the ligands are present at a density of from about 40 to about 80 μmole/ml and from about 0.5 to about 0.8 mmole/g; more preferably at a density of about 50 μmole/ml and about 0.7 mmole/g.

The following Example illustrates the invention.

EXAMPLE

The effect of ligand density on the ratio of binding of BSA:IgG was determined for ABI.

A number of adsorbents were prepared with varying ligand densities. These were prepared via allyl activation (0.1 ml/ml), bromination (using bromine water) and applying controlled levels of ligand (assuming that a 50% coupling efficiency would be achieved) at room temperature. The ligand densities were determined by titration. The media were then decanted and an aliquot taken to determine the ligand densities using tests described in U.S. Pat. Nos. 5,652,348 and 5,945,520.

Capacity measurements were carried out using 1 ml of adsorbent. The adsorbent was equilibrated using 5 column volumes (CV) of PBS buffer. Human polyclonal IgG or bovine serum albumin (BSA) at 40 mg/ml (2.5 ml) was applied to the column, then washed with 5 CV PBS buffer. Elution was carried out using 5 CV of 0.1 M Glycine/HCl (pH2). The capacity was determined by recording the absorption of the eluent at 280 nm.

FIG. 1 shows the effect of ligand density on the ratio of binding of BSA:IgG. It is evident that optimum binding occurs when ABI ligands are used at a density of from about 30 to about 80 μmole/ml. In this case, the optimum ligand density is the density at which the ratio of BSA:IgG is lowest but the IgG capacity is sufficiently high for commercial use.

The invention claimed is:

1. A medium for the isolation of a protein from a solution which comprises a solid support selected from the group consisting of zirconia, polyethylene, polypropylene, polytetrafluoroethylene, polyethersulphone, and polyvinylidene fluoride and, attached thereto, one or more AMBI ligands, wherein the AMBI ligand density is from about from about 40 to about 70 μmole/ml/ml wet and from about 0.5 to about 0.8 mmole/g dry weight.

2. The medium according to claim 1 wherein the AMBI ligand density is about 50 μmole/ml wet and about 0.7 mmole/g dry weight.

3. The medium according to claim 1 wherein the support comprises zirconia.

4. The medium according to claim 1 wherein the support comprises polytetrafluoroethylene.

5. The medium according to claim 1 wherein the support is in the form selected from the group consisting of beads, membranes, non-woven sheets or monolithic structures.

6. A method for isolating a protein from a sample solution, the protein capable of binding to an AMBI ligand, wherein the method comprises contacting the sample with the medium as defined in claim 1.

7. The method according to claim 6 wherein the protein is IgG.

8. A method for the manufacture of the medium of claim 1 comprising applying AMBI ligands at a density of from about from about 40 to about 70 μmole/ml wet and from about 0.5 to about 0.8 mmole/g dry weight to a solid support.

9. The method according to claim 8, wherein the AMBI ligands are applied at a density of from about 50 μmole/ml wet and about 0.7 mmole/g dry weight.

10. A medium for the isolation of IgG from a solution, the medium comprising:
a solid support selected from the group consisting of zirconia, and polytetrafluoroethylene, and, attached thereto, one or more AMBI affinity ligands having a wet ligand density from about from about 40 to about 70 μmole/ml, and a dry ligand density from about 0.5 to about 0.8 mmole/g.

11. The medium according to claim 10 wherein the AMBI ligand density is about 50 μmole/ml wet to about 0.7 mmole/g dry.

12. The medium according to claim 10 wherein the support comprises zirconia.

13. The medium according to claim 10 wherein the support comprises polytetrafluoroethylene.

14. The medium according to claim 10 wherein the support is in the form selected from the group consisting of beads, membranes, non-woven sheets or monolithic structures.

* * * * *